United States Patent [19]

Lackman

[11] Patent Number: 5,582,607
[45] Date of Patent: Dec. 10, 1996

[54] HEART VALVE PROSTHESIS ROTATOR WITH BENDABLE SHAFT AND DRIVE MECHANISM

[75] Inventor: Lamont E. Lackman, Georgetown, Tex.

[73] Assignee: CarboMedics, Inc., Austin, Tex.

[21] Appl. No.: 303,387

[22] Filed: Sep. 9, 1994

[51] Int. Cl.$^6$ ............................................. A61F 2/24
[52] U.S. Cl. .................................... 606/1; 623/2; 623/66
[58] Field of Search ........................ 606/1, 99, 108, 606/205–208; 623/2, 66, 900

[56] References Cited

U.S. PATENT DOCUMENTS

| | | | |
|---|---|---|---|
| 3,628,535 | 12/1971 | Ostrowsky et al. | 606/205 |
| 4,655,218 | 4/1987 | Kulik et al. | 606/205 |
| 4,683,883 | 8/1987 | Martin | 606/1 |
| 4,982,727 | 1/1991 | Sato | 606/205 |
| 5,236,450 | 8/1993 | Scott | 623/66 |
| 5,403,305 | 4/1995 | Sauter et al. | 623/66 |
| 5,443,502 | 8/1995 | Caudillo et al. | 623/2 |

*Primary Examiner*—Angela D. Sykes
*Assistant Examiner*—Michael Peffley
*Attorney, Agent, or Firm*—John R. Merkling

[57] ABSTRACT

A heart valve prothesis rotator which also has an annealed stainless steel shaft which can be bent by the surgeon interoperatively. The shaft will retain its shape after bending. Surrounding the shaft is a drive coil which connects a rotator head at a proximal end of the shaft to a drive knob at a distal end of the shaft and adjacent a handle. By turning the drive knob, a surgeon can turn the rotator head, thus orienting the prosthetic heart valve. Torsional motion is carried along the path defined by the bendable shaft so that the rotator head can be turned without displacing the handle of the heart valve rotator.

20 Claims, 2 Drawing Sheets

HEART VALVE PROSTHESIS ROTATOR WITH BENDABLE SHAFT AND DRIVE MECHANISM

BACKGROUND OF MY INVENTION

1. Field of my Invention

My invention pertains to apparatus for manipulating mechanical heart valve prostheses and in particular to a heart valve prosthesis rotator having a flexible shaft and drive mechanism.

2. Description of Related Art

Heart valve prostheses may be classified into two general categories: bioprosthetic heart valves and mechanical heart valves. By bioprosthetic heart valves, I mean heart valves with generally flexible leaflets comprised of biological tissue. These include leaflets formed of treated human heart valve tissue (allografts), or of treated porcine or other non-human tissue (xenografts). By mechanical heart valves, I mean heart valves made primarily from nonbiologic materials, for example, metals, ceramics or polymers. These include ball valves and valves having one, two or more rigid leaflets. One popular valve design for a mechanical heart valve prosthesis includes an annular valve body in which a pair of opposed leaflet occluders are pivotally mounted. The occluders are movable between a closed, mated position, blocking blood flow in an upstream direction, and minimizing regurgitation, and an open position, allowing blood flow in a downstream direction. The annular valve body is surrounded by a sewing ring which permits the surgeon to suture the valve in place at the site of an excised valve.

When a valve is placed within the heart, it must be accurately oriented to maximize its function. Particularly in mechanical heart valves, the orientation of the leaflets is critical since their opening and closing pathways may otherwise impinge on the surrounding cardiac walls, the walls of arteries within which the valve is placed, or the residual valvular structures including the tendeae chordae and papillary muscles. This difficulty becomes particularly acute in the placement of a heart valve in the position of the mitral valve in the heart. When replacing this valve, a surgeon will frequently expose the posterior side of the patient's heart and enter the heart through the wall of the left atrium and sometimes through the right atrium. It is desirable to place the valve accurately within the cramped confines of the heart while leaving room for the surgeon to sew the valve in place.

In the past, surgeons most often used a left thoracotomy surgical procedure to reach the heart which allows a straight line of access to the mitral valve. Common practice, however, has shifted away from the thoracotomy which involves resecting a rib and provides poor access to the aorta. Many surgeons today perform a median sternotomy, bisecting the rib cage by sawing the sternum in half. This approach provides clear access to the aorta and right atrium, allowing the surgeon to easily place the patient on by-pass, work on the aortic valve and either the pulmonary or tricuspid heart valve. Unfortunately, this approach does not provide easy access to the mitral valve, forcing the surgeon to reach behind the heart or through the right atrium into the left atrium.

To aid in the rotation of the heart valve within a sewing ring in the mitral position, heart valve prosthesis rotators have been proposed heretofore. Some of these rotators have bendable steel shafts which can be bent by the surgeon interoperatively, but which will retain their shape sufficiently to allow the manipulation of a heart valve engaged by the rotator. Such a heart valve rotator has been described be Slaughter, Campbell and Bud in U.S. patent application Ser. No. 08/018,882 which is also assigned to CarboMedics, Inc. the assignee of my invention.

SUMMARY OF MY INVENTION

I have invented a heart valve prothesis rotator which also has an annealed stainless steel shaft which can be bent by the surgeon interoperatively. The shaft will retain its shape after bending. Surrounding the shaft I have provided a drive coil which connects a rotator head at a proximal end of the shaft to a drive knob at a distal end of the shaft and adjacent a handle. By turning the drive knob, a surgeon can turn the rotator head, thus orienting the prosthetic heart valve. Torsional motion is carried along the path defined by the bendable shaft so that the rotator head can be turned without displacing the handle of the heart valve rotator.

With the foregoing in mind, it is a principal object of my invention to provide a heart valve prosthesis rotator with a deformable shaft and drive coil.

It is a further object of my invention to provide a heart valve rotator with a rotator head that can be turned without displacing a handle of the rotator, thus providing well-controlled manipulation of the heart valve.

These and other objects and features of my invention will be apparent to those skilled in the art from the following detailed description of my preferred embodiment taken with reference to the accompanying drawings.

DETAILED DESCRIPTION OF MY PREFERRED EMBODIMENT

Figure 1:
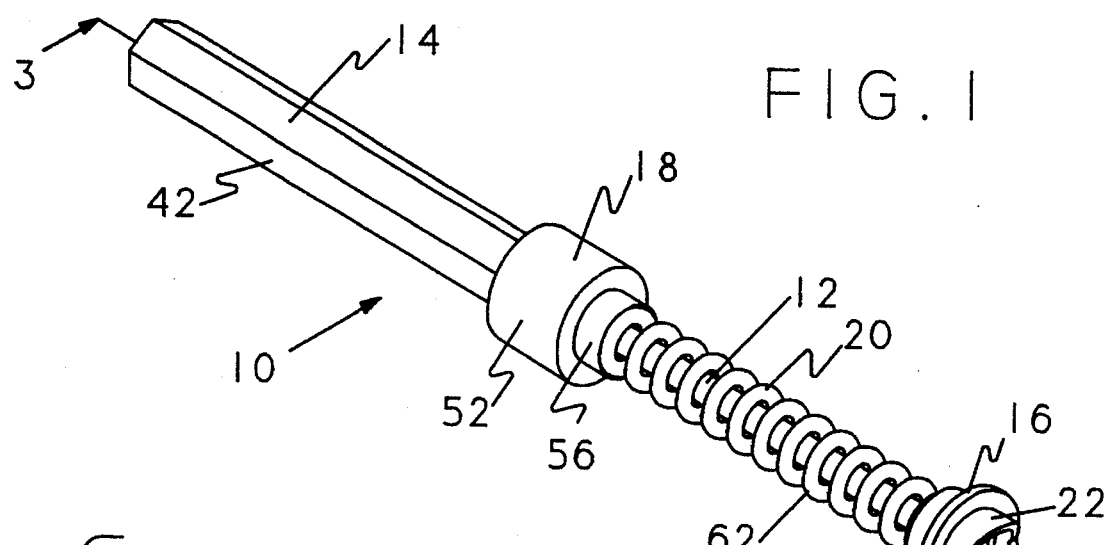
FIG. 1 perspective view of a heart valve rotator according to my invention.

Referring now to the drawings, a heart valve prosthesis rotator, generally designated 10, is shown in perspective view in FIG. 1. The rotator 10 comprises an annealed stainless steel shaft 12 with a plastic handle 14 at a distal end thereof. "Proximal" denotes a part of an apparatus which is relatively close to the heart when in use, as is customary in cardiovascular surgery. "Distal" denotes a part remoted from the heart and, consequently, near the physician. At a proximal end of the shaft 12 there is a rotator head 16. At a proximal end of the handle 14, there is a drive knob 18. A drive coil 20 connects the drive knob 18 to the rotator head 16.

Mechanical heart valves generally comprise an annular body containing one, two or more leaflets or occluders. Leaflets move from a closed position impeding the flow of blood to an open position, permitting flow of blood. In my preferred embodiment, the rotator head 16 is described. With a configuration for a bileaflet mechanical heart valve for use in the mitral position in the heart. Those skilled in the art, however, will recognized that rotator heads may be constructed for single leaflet valves as well as for trileaflet or multiple leaflet valves and for the mitral or atrial positions without departing from the spirit or teachings of my invention.

Figure 2:
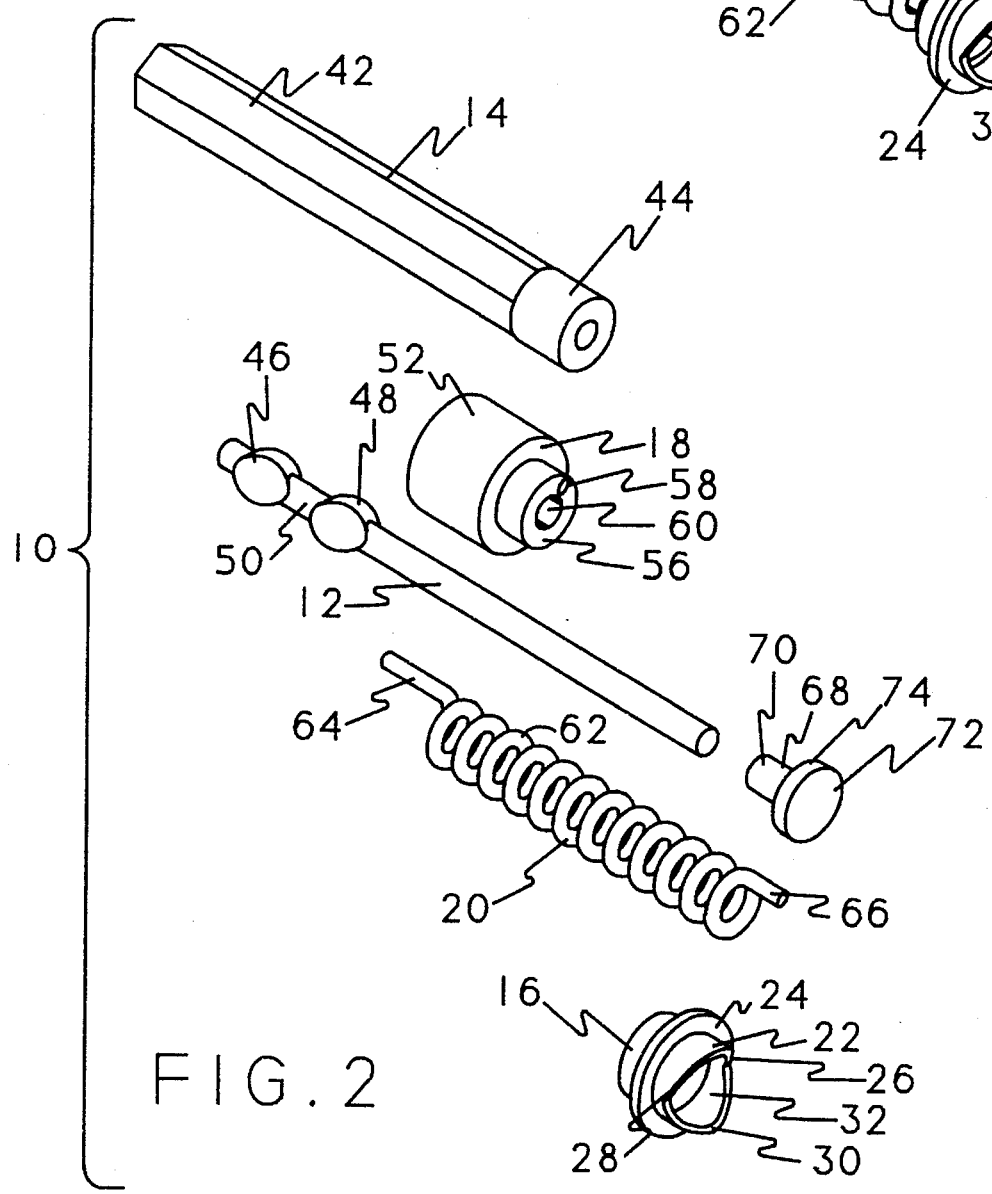
FIG. 2 is an exploded perspective view of the heart valve rotator of FIG. 1.
Figure 3:
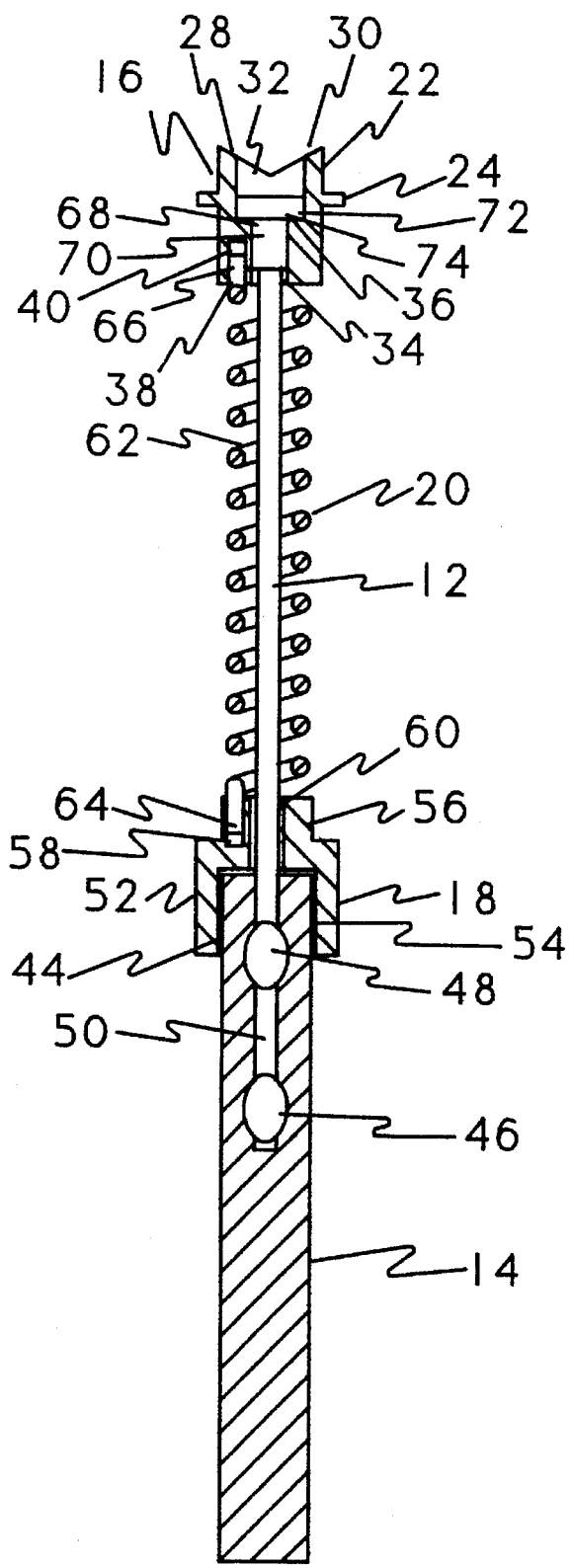
FIG. 3 is a through section of the heart valve rotator of FIG. 1, taken along line 3—3.

The rotator head 16 is shown in perspective view both in FIGS. 1 and 2 and in through section in FIG. 3. The rotator head 16 comprises a generally cylindrical body 22 having a annular lip 24. The annular lip 24 will engage the annular body of a heart valve. At a proximal end 26 of the cylindrical body 22 are surfaces 28, 30 for engaging the leaflets of a bileaflet heart valve. The two surfaces 28, 30 meet at an obtuse included angle in configurations for use with a bileaflet mitral heart valve. For a bileaflet atrial valve, of course, the angle at which the two surfaces meet would be greater that 180 degrees, that is, the most proximal part of the heart valve of the rotator head would be the points where the two surfaces 28, 30 meet. Other configurations would be adopted for single leaflet or trileaflet valves, the configuration of these surfaces being dictated by the configuration of the valve to be manipulated.

There is a proximal bore 32 extending from the proximal end 26 of the rotator head into the rotator head 16. Coaxially with the proximal bore 32 there is a distal bore 34, which has a smaller diameter than the proximal bore. These two bores 32, 34 meet within the rotator head 16, forming a circumferential ledge 36. At a distal end 38 of the rotator head 16, there is a offset stopped bore for engaging the drive coil 12, as will be more particularly described hereafter.

In my preferred embodiment, the handle 14 is formed of plastic and can be molded around the bendable shaft 12 so that the handle 14 and the shaft 12 are securely attached to one another. The handle 14 has a distal grip 42 with suitable features to provide a secure grip for the surgeon. I have illustrated a hexagonal shape for the grip 42, but other suitable shapes could also be chosen. Proximally on the handle 14, there is a cylindrical section 44 about which the drive knob 18 turns. The shaft 12, preferably composed of an annealed stainless steel, has two flats 46, 48 provided at a distal end 50 thereof. Preferably, the handle 14 is molded around the shaft 12 with the flats 46, 48 within the handle. This provides a secure connection between the shaft 12 and the handle 14.

The drive knob 18 comprises a collar 52 which has an internal cavity 54, sized to fit over the cylindrical section 44 of the handle 14. Proximally from the collar 52 is a cylindrical neck 56 having an offset stopped bore 58 which engages the drive coil 12, as will be more fully described below. A central through bore 60 extends through the neck 56 into the cavity 54. The shaft 12 passes through this bore 60 and the drive knob 18 can, therefore, be rotated about the cylindrical section 44 of the handle 14 and the shaft 12. The drive coil 20 essentially comprises a coiled spring 62 which fits around the shaft 12. At each end of the spring 62 there is a tang. A distal tang 64 fits into the stopped bore 58 of the drive knob 18. A proximal tang 66 fits into the stopped bore 40 in the rotator head 16. Thus, turning the drive knob 18 will impart torsional motion through the drive coil 12 to the rotator head 16 without significant motion of the handle 14. This is true even if the shaft 12 has been bent into a nonlinear shape. The drive coil 12 will be able to follow that shape and still transfer the torsional motion to the rotator head.

The drive knob 18, drive coil 12 and rotator head 16 are held on the handle 14 and shaft 12 by a retainer 68. The retainer 68 comprises a cylinder 70 with a internal bore which fits over the proximal end of the shaft 12. A press fit is used to attach the retainer to the end of the shaft 12. Of course, other methods of securing the retainer 68 could also be selected, such as threads or adhesive. A cap 72 forms a circumferential lip 74 which engages the ledge 36 formed by the intersection of the proximal bore 32 and the distal bore 34 in the rotator head.

After a heart valve has been initially stitched into an appropriate location within the heart, the heart rotator of my invention can be used to orient the annular body of the heart valve within its sewing ring, thus orienting the leaflets. By bending the shaft 12, the surgeon can bring the rotator head into appropriate contact with the heart valve despite limitations imposed by the physiology of a patient or by the surgical techniques selected for implanting the valve. By turning the drive knob 18, the surgeon can then turn the annular body of the valve to any desired orientation.

My invention may be embodied in other specific forms without departing from the spirit or other essential characteristics thereof. The foregoing description is, therefore, to be viewed in all respects as illustrative and not restrictive. The scope of my invention is defined by the appended claims, and all varients within the scope of equivalency of the claims are intended to be included therein.

I claim as my invention:

1. A rotator for a mechanical heart valve comprising a handle, a shaft attached to a proximal end of said handle, a rotator head adapted to engage an annular valve body within said mechanical heart valve, said rotator head being rotatably attached to a proximal end of said shaft, and a coil attached to said rotator head and extending along said shaft for turning said rotator head.

2. The rotator according to claim 1 further comprising a knob secured to a distal end of said coil.

3. The rotator according to claim 2 wherein said knob is rotatably secured around said shaft adjacent said proximal end of said handle.

4. The rotator according to claim 3 wherein said rotator head has an internal bore and said shaft has retainer means at said proximal end thereof for securing said rotator head, said retainer means being within said bore.

5. The rotator according to claim 4 wherein said rotator head further comprises at least one surface for engaging at least one leaflet in said mechanical heart valve.

6. The rotator according to claim 1 wherein said shaft is bendable.

7. The rotator according to claim 6 further comprising a knob secured to a distal end of said coil.

8. The rotator according to claim 7 wherein said knob is rotatably secured around said shaft adjacent said proximal end of said handle.

9. The rotator according to claim 8 wherein said rotator head has an internal bore and said shaft has retainer means at said proximal end thereof for securing said rotator head, said retainer means being within said bore.

10. The rotator according to claim 9 wherein said rotator head further comprises at least one surface for engaging at least one leaflet in said mechanical heart valve.

11. A rotator for a mechanical heart valve comprising a handle, a shaft attached to a proximal end of said handle, means at a proximal end of said shaft for engaging an annular valve body within said mechanical heart valve, and means for turning said means for engaging without turning said handle or said shaft.

12. The rotator according to claim 11 further comprising means for manually gripping said means for turning.

13. The rotator according to claim 12 wherein said means for gripping is rotatably secured around said shaft adjacent said proximal end of said handle.

14. The rotator according to claim 13 wherein said shaft has means at said proximal end thereof for rotatably securing said means for engaging to said proximal end of said shaft.

15. The rotator according to claim 14 wherein said means for engaging further comprises at least one surface for supporting at least one leaflet in said mechanical heart valve.

16. The rotator according to claim 11 wherein said shaft is bendable.

17. The rotator according to claim 16 further comprising means for manually gripping said means for turning.

18. The rotator according to claim 17 wherein said means for gripping is rotatably secured around said shaft adjacent said proximal end of said handle.

19. The rotator according to claim 18 wherein said shaft has means at said proximal end thereof for rotatably securing said means for engaging to said proximal end of said shaft.

20. The rotator according to claim 19 wherein said means for engaging further comprises at least one surface for supporting at least one leaflet in said mechanical heart valve.

* * * * *